United States Patent
Konwitz et al.

(10) Patent No.: US 11,426,061 B2
(45) Date of Patent: *Aug. 30, 2022

(54) COMPACT ENDOSCOPE TIP AND METHOD FOR CONSTRUCTING SAME

(71) Applicant: Cogentix Medical, Inc., Minnetonka, MN (US)

(72) Inventors: Ellie Konwitz, Ramat-Gan (IL); Martin Abraham, Hod-HaSharon (IL); Thomas S. Soulos, New York, NY (US); Ron Hadani, Creskill, NJ (US)

(73) Assignee: COGENTIX MEDICAL, INC., Minnetonka, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/793,663

(22) Filed: Feb. 18, 2020

(65) Prior Publication Data

US 2020/0178777 A1  Jun. 11, 2020

Related U.S. Application Data

(63) Continuation of application No. 16/352,246, filed on Mar. 13, 2019, now Pat. No. 10,588,497, which is a continuation of application No. 12/230,745, filed on Sep. 4, 2008, now Pat. No. 10,244,928.

(60) Provisional application No. 60/935,891, filed on Sep. 5, 2007.

(51) Int. Cl.
*A61B 1/05* (2006.01)
*A61B 1/00* (2006.01)

(52) U.S. Cl.
CPC ............ *A61B 1/05* (2013.01); *A61B 1/00096* (2013.01); *A61B 1/051* (2013.01); *Y10T 29/49826* (2015.01)

(58) Field of Classification Search
CPC ..... A61B 1/0008; A61B 1/00105; A61B 1/05; A61B 1/00096; A61B 1/051
See application file for complete search history.

(56) References Cited

U.S. PATENT DOCUMENTS

| | | |
|---|---|---|
| 4,040,413 A | 8/1977 | Ohshiro |
| 4,364,629 A | 12/1982 | Lang et al. |
| 4,406,656 A | 9/1983 | Horgan et al. |
| 4,545,367 A | 10/1985 | Tucci |

(Continued)

FOREIGN PATENT DOCUMENTS

| | | |
|---|---|---|
| EP | 1187549 A1 | 3/2002 |
| EP | 2011431 A1 | 1/2009 |

(Continued)

OTHER PUBLICATIONS

"Response to Jul. 19, 2011 Communication Pursuant to Article 94(3)", Application No. 04780129.5, dated Nov. 17, 2011, 6 pages.

(Continued)

*Primary Examiner* — Matthew J Kasztejna
(74) *Attorney, Agent, or Firm* — Dorsey & Whitney LLP

(57) ABSTRACT

This application presents to an endoscope having a compact distal tip, and to a method for constructing same. In some embodiments one or more optical and sensing elements are mounted directly on an internal surface of a lumen within an external housing, which housing comprises an outer wall of the endoscope tip. Space saved by eliminating intervening containing elements can be used to enhance endoscope performance and/or reduce endoscope size.

20 Claims, 3 Drawing Sheets

(56) References Cited

U.S. PATENT DOCUMENTS

| | | |
|---|---|---|
| 4,622,954 A | 11/1986 | Arakawa et al. |
| 4,646,722 A | 3/1987 | Silverstein et al. |
| 4,676,228 A | 6/1987 | Krasner et al. |
| 4,773,396 A | 9/1988 | Okazaki |
| 4,830,460 A | 5/1989 | Goldenberg |
| 4,841,952 A | 6/1989 | Sato et al. |
| 4,856,495 A | 8/1989 | Tohjoh et al. |
| 4,881,810 A | 11/1989 | Hasegawa |
| 5,025,778 A | 6/1991 | Silverstein et al. |
| 5,051,824 A | 9/1991 | Nishigaki |
| 5,083,549 A | 1/1992 | Cho et al. |
| 5,166,787 A | 11/1992 | Irion |
| 5,167,220 A | 12/1992 | Brown |
| 5,201,908 A | 4/1993 | Jones |
| 5,217,001 A | 6/1993 | Nakao et al. |
| 5,305,736 A | 4/1994 | Ito |
| 5,373,845 A | 12/1994 | Gardineer et al. |
| 5,377,688 A | 1/1995 | Aviv et al. |
| 5,379,756 A | 1/1995 | Pileski et al. |
| 5,460,168 A | 10/1995 | Masubuchi et al. |
| 5,483,951 A | 1/1996 | Frassica et al. |
| 5,489,256 A | 2/1996 | Adair |
| 5,503,616 A | 4/1996 | Jones |
| 5,547,457 A | 8/1996 | Tsuyuki et al. |
| 5,588,432 A | 12/1996 | Crowley |
| 5,734,418 A | 3/1998 | Danna |
| 5,749,889 A | 5/1998 | Bacich et al. |
| 5,810,776 A | 9/1998 | Bacich et al. |
| 5,823,940 A | 10/1998 | Newman |
| 5,842,973 A | 12/1998 | Bullard |
| 5,871,440 A | 2/1999 | Okada |
| 5,898,185 A | 4/1999 | Bojarczuk, Jr. et al. |
| 5,940,126 A | 8/1999 | Kimura |
| 5,961,445 A | 10/1999 | Chikama |
| 5,966,168 A | 10/1999 | Miyazaki |
| 5,989,185 A | 11/1999 | Miyazaki |
| 6,095,970 A | 8/2000 | Hidaka et al. |
| 6,146,326 A | 11/2000 | Pollack et al. |
| 6,174,280 B1 | 1/2001 | Oneda et al. |
| 6,328,691 B1 | 12/2001 | Rudischhauser |
| 6,358,200 B1 | 3/2002 | Grossi |
| 6,361,491 B1 | 3/2002 | Hasegawa et al. |
| 6,443,968 B1 | 9/2002 | Holthaus et al. |
| 6,461,294 B1 | 10/2002 | Oneda et al. |
| 6,579,301 B1 | 6/2003 | Bales et al. |
| 6,692,431 B2 | 2/2004 | Kazakevich |
| 6,740,030 B2 | 5/2004 | Martone et al. |
| 6,761,685 B2 | 7/2004 | Adams et al. |
| 6,808,520 B1 | 10/2004 | Fourkas et al. |
| 6,827,710 B1 | 12/2004 | Mooney et al. |
| 7,044,135 B2 | 5/2006 | Lesh |
| 7,410,462 B2 | 8/2008 | Navok et al. |
| 7,435,218 B2 | 10/2008 | Krattiger et al. |
| 7,645,229 B2 | 1/2010 | Armstrong |
| 7,753,842 B2 | 7/2010 | Glukhovsky et al. |
| 7,878,972 B2 | 2/2011 | D et al. |
| 7,883,468 B2 | 2/2011 | Makin et al. |
| 8,002,699 B2 | 8/2011 | Hoefig |
| 8,435,170 B2 | 5/2013 | Wood et al. |
| 8,568,300 B2 | 10/2013 | Navok et al. |
| 8,692,874 B2 | 4/2014 | Adler et al. |
| 9,820,719 B2 | 11/2017 | Hadani et al. |
| 10,244,928 B2 | 4/2019 | Konwitz et al. |
| 2001/0000040 A1 | 3/2001 | Adams et al. |
| 2001/0047135 A1 | 11/2001 | Daniels et al. |
| 2002/0062083 A1 | 5/2002 | Ohara et al. |
| 2003/0114878 A1 | 6/2003 | Diederich et al. |
| 2003/0130564 A1 | 7/2003 | Martone et al. |
| 2003/0153833 A1 | 8/2003 | Bennett et al. |
| 2003/0167023 A1 | 9/2003 | Bennett et al. |
| 2004/0019254 A1 | 1/2004 | Belson et al. |
| 2004/0082859 A1 | 4/2004 | Schaer |
| 2004/0082883 A1 | 4/2004 | Kohno |
| 2004/0092821 A1 | 5/2004 | Hering et al. |
| 2004/0143162 A1 | 7/2004 | Krattiger et al. |
| 2004/0230095 A1 | 11/2004 | Stefanchik et al. |
| 2004/0230096 A1 | 11/2004 | Stefanchik et al. |
| 2005/0049455 A1 | 3/2005 | Ootawara et al. |
| 2005/0131278 A1 | 6/2005 | Dickopp |
| 2005/0182299 A1 | 8/2005 | D et al. |
| 2005/0261586 A1 | 11/2005 | Makin et al. |
| 2005/0277808 A1 | 12/2005 | Sonnenschein et al. |
| 2006/0020171 A1 | 1/2006 | Gilreath |
| 2006/0149127 A1 | 7/2006 | Seddiqui et al. |
| 2006/0264705 A1 | 11/2006 | Adams et al. |
| 2007/0038089 A1 | 2/2007 | Hatano et al. |
| 2007/0203396 A1 | 8/2007 | Mccutcheon et al. |
| 2007/0249940 A1 | 10/2007 | Kohno |
| 2007/0265494 A1 | 11/2007 | Leanna et al. |
| 2007/0293719 A1 | 12/2007 | Scopton et al. |
| 2008/0004528 A1 | 1/2008 | Fitzsimons et al. |
| 2009/0318797 A1 | 12/2009 | Hadani |
| 2010/0042112 A1 | 2/2010 | Qureshi et al. |
| 2010/0125164 A1 | 5/2010 | Labombard |
| 2011/0152618 A1 | 6/2011 | Surti |
| 2012/0089028 A1 | 4/2012 | Hadani et al. |
| 2014/0364691 A1 | 12/2014 | Krivopisk et al. |
| 2015/0031947 A1 | 1/2015 | Kudo et al. |
| 2018/0070918 A1 | 3/2018 | Hadani et al. |
| 2019/0208999 A1 | 7/2019 | Konwitz et al. |

FOREIGN PATENT DOCUMENTS

| | | |
|---|---|---|
| GB | 2336540 A | 10/1999 |
| JP | 3429536 B2 | 9/1993 |
| WO | 9518562 A1 | 7/1995 |
| WO | 0071016 A1 | 11/2000 |
| WO | 2005016181 A2 | 2/2005 |
| WO | 2007103296 A2 | 9/2007 |
| WO | 2007103355 A1 | 9/2007 |

OTHER PUBLICATIONS

"Response to Feb. 21, 2011 Communication Pursuant to Article 94(3)", Application No. 04780129.5, dated Jun. 15, 2011, 6 pages.

Ehrlich & Fenster, "Response to Jun. 10, 2010 Proceedings Further With the European Patent App. Pursuant to Rule 70(2)", Application No. 04780129.5, dated Aug. 8, 2010, 6 pages.

Ehrlich & Fenster, "Response to Jul. 19, 2010 Communication Pursuant to Article 94(3) EPC", Application No. 08163701.9, dated Nov. 18, 2010, 13 pages.

Ehrlich & Fenster, "Response to Sep. 25, 2009 Communication Pursuant to Article 94(3) EPC", Application No. 08163701.9, dated Jan. 26, 2010, 9 pages.

Ehrlich & Fenster, "Response to Sep. 9, 2011 Communication Pursuant to Article 94(3) EPC", Application No. 08163701.9, dated Jan. 9, 2012, 11 pages.

"Communication Pursuant to Article 94(3)", Application No. 04780129.5, dated Jul. 19, 2011, 7 pages.

"Communication Pursuant to Article 94(3)", Application No. 04780129.5, dated Feb. 21, 2011, 9 pages.

"Communication Pursuant to Article 94(3) EPC", Application No. 08163701.9, dated Jul. 5, 2013, 3 pages.

"Communication Pursuant to Article 94(3) EPC", Application No. 08163701.9, dated Sep. 9, 2011, 3 pages.

"Communication Pursuant to Article 94(3) EPC", Application No. 08163701.9, dated Jun. 5, 2012, 4 pages.

"Communication Pursuant to Article 94(3) EPC", Application No. 08163701.9, dated Jul. 19, 2010, 4 pages.

"Communication Pursuant to Article 94(3) EPC", Application No. 08163701.9, dated Aug. 6, 2014, 4 pages.

"Communication Pursuant to Article 94(3) EPC", Application No. 08163701.9, dated Sep. 25, 2009, 4 pages.

"Extended European Search Report", Application No. 14198653.9, dated Mar. 27, 2015, 8 pages.

"Notification of European Publication Number and Information on the Application of Article 67(3) EPC", Application No. 14198653.9, dated Apr. 1, 2015, 2 pages.

"Proceeding Further with the European Patent App. Pursuant to Rule 70(2) EPC", Application No. 04780129.5, dated Jun. 10, 2010, 2 pages.

(56) References Cited

OTHER PUBLICATIONS

"Search Report", Application No. 08163701.9, dated Oct. 21, 2008, 5 pages.
"Summons to Attend Oral Proceedings Pursuant to Rule 115(1) EPC", Application No. 04780129.5, dated Apr. 1, 2015, 7 pages.
"Supplementary European Search Report", Application No. 04780129.5, dated Apr. 20, 2010, 3 pages.
Nederlandsch Octrooibureau, "Response to Jul. 19, 2011 Communication Pursuant to Article 94(3)", Application No. 04780129.5, dated Nov. 21, 2011, 10 pages.
Nederlandsch Octrooibureau, "Response to Feb. 21, 2011 Communication Pursuant to Article 94(3)", Application No. 04780129.5, dated Jun. 27, 2011, 11 pages.
Olympus Corporation, "Evis Exera Duodenovideoscope Olympus TJF Type 160VF", Product Description; LinearGuideV, 2 pages.
"Inernational Search Report", Application No. PCT/IL07/00204, dated Sep. 8, 2008, 5 pages.
"International Preliminary Report on Patentability", Application No. PCT/US2004/025238, dated Feb. 15, 2006, 14 pages.
"International Search Report and Written Opinion", Application No. PCT/US2016/042062, dated Oct. 4, 2016, 10 pages.
"International Search Report and Written Opinion", Patent Application No. PCT/US2004/025238, dated Feb. 14, 2005, 7 pages.
"Final Office Action", U.S. Appl. No. 12/486,795, filed Jan. 25, 2013, 11 pages.
"Final Office Action", U.S. Appl. No. 12/486,795, filed Feb. 7, 2014, 16 pages.
"Non-Final Office Action", U.S. Appl. No. 13/330,950, filed Dec. 13, 2013, 12 pages.
"Non-Final Office Action", U.S. Appl. No. 12/486,795, filed Aug. 20, 2013, 13 pages.
"Non-Final Office Action", U.S. Appl. No. 12/486,795, filed Apr. 27, 2012, 17 pages.
"Restriction Official Action", U.S. Appl. No. 12/486,795, filed Feb. 29, 2012, 8 pages.

COMPACT ENDOSCOPE TIP AND METHOD FOR CONSTRUCTING SAME

CROSS-REFERENCE TO RELATED APPLICATIONS

This application is a continuation of U.S. patent application Ser. No. 16/352,246, filed Mar. 13, 2019, now U.S. Pat. No. 10,588,497, which in turn is a continuation of U.S. patent application Ser. No. 12/230,745, filed Sep. 4, 2008, now U.S. Pat. No. 10,244,928, which claims priority to U.S. Provisional Patent Application No. 60/935,891, filed Sep. 5, 2007, each of which is incorporated by reference herein, in the entirety and for all purposes.

FIELD OF THE INVENTION

The present invention, in some embodiments thereof, relates to an endoscope and, more particularly, but not exclusively, to an endoscope having a compact distal tip, and to a method for constructing same.

BACKGROUND OF THE INVENTION

Endoscopes are an essential tool in minimally invasive diagnosis and surgery. The maneuverability of an endoscope and it's suitability for accessing small and delicate regions of the body are in part determined by the size of the endoscope tip, which in turn is determined by the sizes of various components the tip contains. An endoscope tip may comprise an objective lens package containing lenses and spacers in a container, a prism, an imaging sensor array, and a plurality of lumens for containing fiberoptic bundles used for illumination, for transmitting fluid used for irrigation, for insufflation, for lens cleaning, or other purposes, and/or serving as working channels for delivering diagnostic and surgical tools to an intervention site.

U.S. Pat. No. 5,305,736 to Ito and U.S. Pat. No. 4,773,396 to Okazaki describe exemplary endoscope tip designs according to the methods of prior art, wherein camera and associated lenses are mounted together within an imaging housing, and that housing is placed within an endoscope tip.

Note is also taken of PCT publication WO 2006/080015, by Pinchas Gilboa entitled "Endoscope with Miniature Imaging Arrangement", which describes another method of mounting lenses within a tip of a flexible endoscope.

Note is also taken of U.S. Pat. No. 5,418,566 to Kameishi, which describes an imaging apparatus for an endoscope, and of U.S. Pat. No. 5,188,092 to White, dated Feb. 23, 1993, which describes a rigid endoscope construction.

Disclosures of all the aforementioned patents and patent applications are incorporated herein by reference.

SUMMARY OF THE INVENTION

Embodiments of the present invention relate to a compact endoscope tip wherein optical and other components are mounted directly into an external housing, thereby enabling small endoscope tip size and/or enhanced endoscope performance.

According to an aspect of some embodiments of the present invention there is provided an endoscope tip comprising an external housing which comprises an outer wall of the endoscope tip; and a lumen; and a first optical element mounted directly on an internal surface of the lumen.

According to some embodiments of the invention the external housing is of unitary construction.

According to some embodiments of the invention, the external housing is of split construction and is openable to provide access to an internal lumen of the housing during fabrication of the endoscope tip.

According to some embodiments of the invention, the endoscope tip further comprises a second optical element positioned by being mounted in flush contact with the first optical element.

According to some embodiments of the invention, an initial optical element, a plurality of intermediate optical elements and a final optical element are serially positioned along a length of an internal lumen of the housing, the length of internal lumen being sized and positioned to accommodate and to align the optical elements.

According to some embodiments of the invention, the initial and final optical elements are attached to an internal wall of the lumen.

According to some embodiments of the invention, only the initial and final optical elements are attached to walls of the lumen, the plurality of intermediate optical elements being unattached to the lumen and maintained in place by walls of the lumen and by the initial and final elements.

According to some embodiments of the invention, the final optical element is positioned against a stop within the lumen, and the first optical element is attached to an internal wall of the length of the lumen.

According to some embodiments of the invention, of the optical elements, only the final optical element is attached the lumen, the plurality of intermediate optical elements being unattached to the lumen and maintained in place by walls of the lumen and by the initial and final elements.

According to some embodiments of the invention, the initial, intermediate, and final optical elements comprise an objective lens array.

According to some embodiments of the invention, an optical sensor array is mounted directly on an internal surface of a lumen within the external housing According to some embodiments of the invention, there is provided a visualization system with a plurality of components, and a lumen of the housing comprises a shaped portion, the shaped portion being shaped to conform to a shape of a visualization system component and being so positioned and oriented that the visualization system component is aligned with an optical axis of the visualization system when the visualization system is installed in the housing and the component is mounted flush against the shaped portion.

According to some embodiments of the invention, the shaped portion is formed as a flat shelf surface, and the visualization system element is an optical sensor array.

According to some embodiments of the invention, the endoscope tip comprises a plurality of shaped lumen portions, each of the shaped portions being individually shaped to conform to a shape of a one of the visualization system components, the plurality of shaped portions being so positioned and oriented that when each of the plurality of visualization system components is mounted on a selected one of the shaped lumen portions, then the visualization system components are optically and functionally aligned with each other.

According to some embodiments of the invention, an objective lens array is installed within a lumen of the housing, at least some light-transmissive elements of the array being in direct contact with walls of the lumen.

According to some embodiments of the invention, the objective lens array comprises a plurality of lenses and at least one spacer.

According to some embodiments of the invention, a distal portion of a fiberoptic bundle is mounted within a lumen of the housing and attached directly to the housing.

According to some embodiments of the invention, the fiberoptic bundle is a coherent fiberoptic bundle.

According to an aspect of some embodiments of the present invention there is provided a method for manufacturing an endoscope tip, comprising:

(a) fabricating a housing which comprises at least one lumen sized to receive at least one component of a multi-component visualization system, the lumen comprising a portion shaped to orient the received component with respect to an optical axis of the visualization system; and (b) installing within the housing a visualization system which comprises a plurality of components arranged with respect to an optical axis, where the installation process comprises mounting at least one component in the shaped portion of the lumen, thereby orienting the component with respect to the optical axis of the visualization system.

According to some embodiments of the invention, the method further comprises mounting a series of optical elements within a lumen of the housing by (a) attaching a first element of the series of elements within the lumen;

(b) introducing at least one additional element into the lumen so that the introduced elements are contiguous; and (c) introducing a final element into the lumen and attaching it to the lumen.

According to some embodiments of the invention, the first and the final elements of the optical elements are attached to the lumen, and the additional elements are unattached.

According to some embodiments of the invention, the method further comprises mounting a series of optical elements within a lumen of the housing by (a) introducing a first element of the series of elements into the lumen and advancing it within the lumen until it is stopped by contact with a form established within the lumen;

(b) introducing at least one additional element into the lumen so that the introduced elements are contiguous; and (c) introducing a final element into the lumen and attaching it to the lumen.

According to some embodiments of the invention, the final element of the optical elements is attached to the lumen, and the first and the additional elements are unattached.

According to some embodiments of the invention, the method further comprises attaching a light sensor array to a shelf within a lumen of the housing.

According to some embodiments of the invention, attaching of the light sensor array comprises verification of alignment and focus along one axis only.

According to some embodiments of the invention, the housing comprises a plurality of lumen portions each sized and shaped to receive a component of a multi-component visualization system, and wherein when a plurality of the components are mounted in the plurality of shaped lumen portions, the components are optically aligned with one another.

According to an aspect of some embodiments of the present invention there is provided an endoscope tip comprising:

(a) an external housing which comprises
   (i) an outer wall of the endoscope tip; and
   (ii) a lumen; and (b) an optical sensor array mounted directly on an internal surface of the lumen.

According to an aspect of some embodiments of the present invention there is provided an endoscope tip comprising:

(a) a visualization system which comprises a plurality of components; and (b) an external housing which comprises
   (i) an outer wall of the endoscope tip; and
   (ii) a lumen which comprises a shaped portion, the shaped portion being shaped to conform to a shape of a component of the visualization system and being so positioned and oriented that the visualization system component is aligned with an optical axis of the visualization system when the visualization system is installed in the housing and the component is mounted flush against the shaped portion.

According to some embodiments of the invention the shaped portion is formed as a flat shelf surface, and the visualization system element is an optical sensor array.

According to some embodiments of the invention the endoscope tip further comprises a plurality of shaped lumen portions, each of the shaped portions being individually shaped to conform to a shape of a one of the visualization system components, the plurality of shaped portions being so positioned and oriented that when each of the plurality of visualization system components is mounted on a selected one of the shaped lumen portions, then the visualization system components are optically and functionally aligned with each other.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
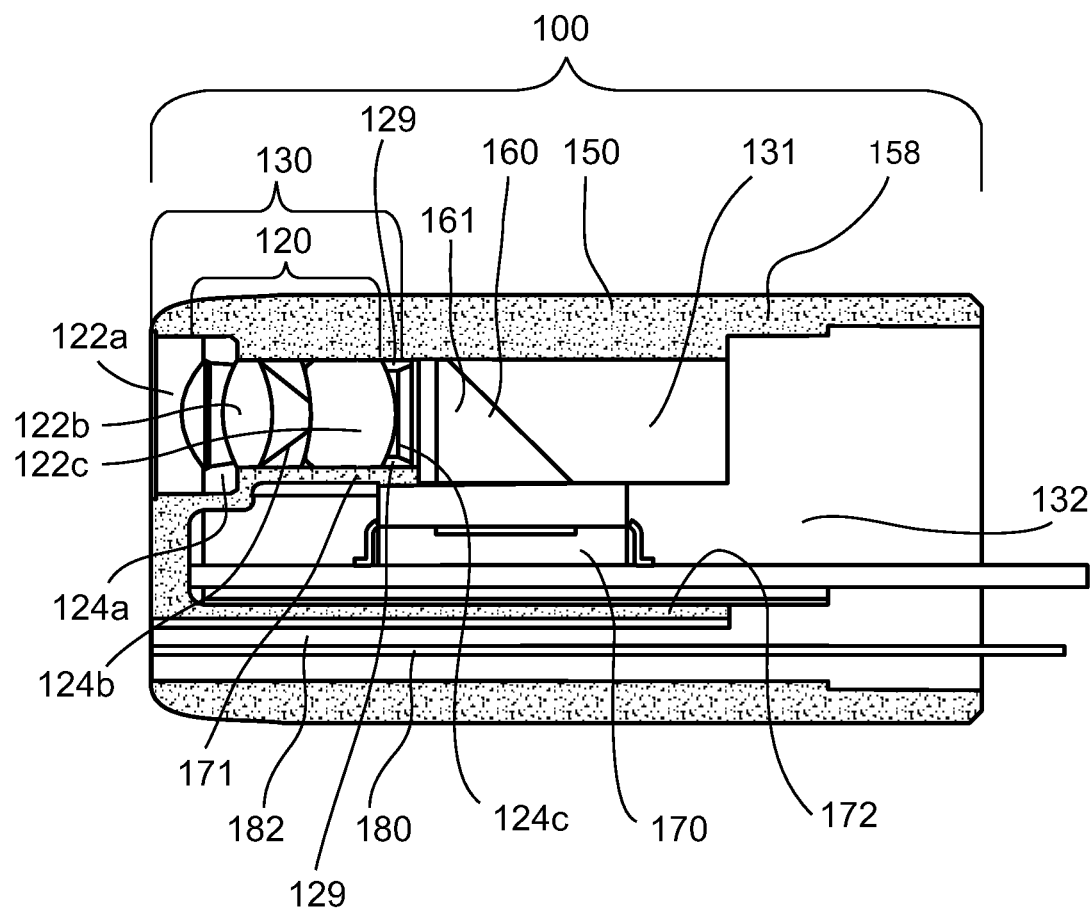
FIG. 1 is a simplified schematic of a cross-sectional side view of an endoscope tip, according to an embodiment of the present invention.

The present invention, in some embodiments thereof, relates to an endoscope and, more particularly, but not exclusively, to an endoscope having a compact distal tip, and to a method for constructing same.

Embodiments here presented include endoscopes having distal tips of reduced cross-sectional size. The endoscope distal tip is a complex portion of the endoscope, having many internal parts. A tip may contain a camera and associated lenses, passages for optical fibers used for illuminating tissues in the vicinity of the endoscope tip, LEDs for illuminating the work area, fluid channels for irrigation and/or inflation, and optionally one or more operating channels for delivering tools to a treatment area.

In embodiments presented herein, reduction in cross-sectional size of endoscope tips is accomplished by mounting optical and/or electronic components directly into appropriately sized and shaped lumens manufactured within an endoscope tip housing, eliminating (as compared to prior art methods) various intermediary subassembly frames and containers and connecting and mounting surfaces.

Construction methods taught herein save space which in prior art methods of construction is taken up by subassembly containers. Space saved by mounting components directly into a tip housing, without intermediary subassemblies and other objects, enables making endoscopes with smaller cross-sectional areas. Endoscopes with tips having smaller cross-sections are more easily maneuverable within patients and are able to access smaller internal structures of the anatomy. Alternately, space saved can be used to enhance endoscope performance, for example by providing, for a same cross-sectional area as a prior-art endoscope, higher-resolution imaging sensor arrays and/or larger optical elements and/or larger optical fibers for illumination and/or larger LEDs for illumination and/or larger lumens for fluid or instrument delivery.

Additionally, by use of methods here presented, endoscope tip construction is simplified, duplication of effort is avoided, and calibration of optical components is simplified. Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Figure 2:
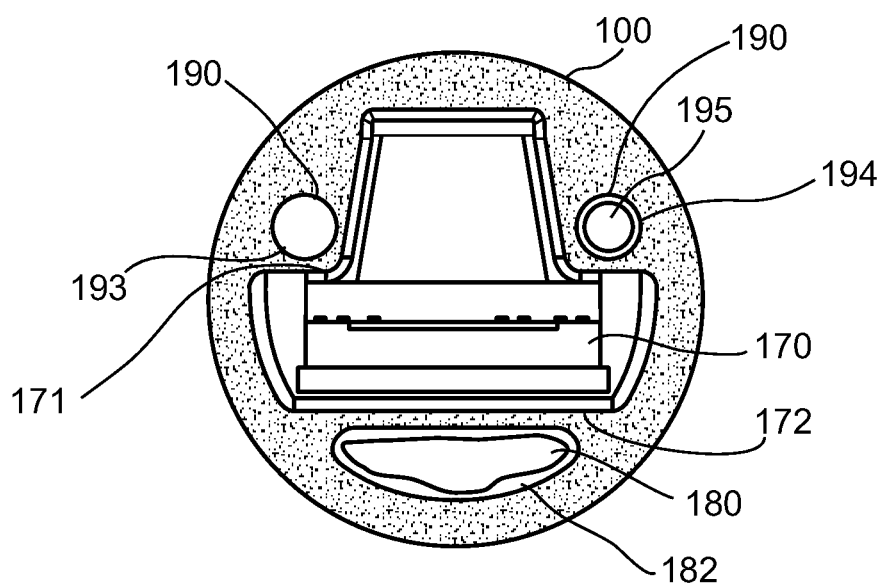
FIG. 2 is a simplified schematic of a cross-sectional rear view of the endoscope tip of FIG. 1, according to an embodiment of the present invention.
Figure 3:
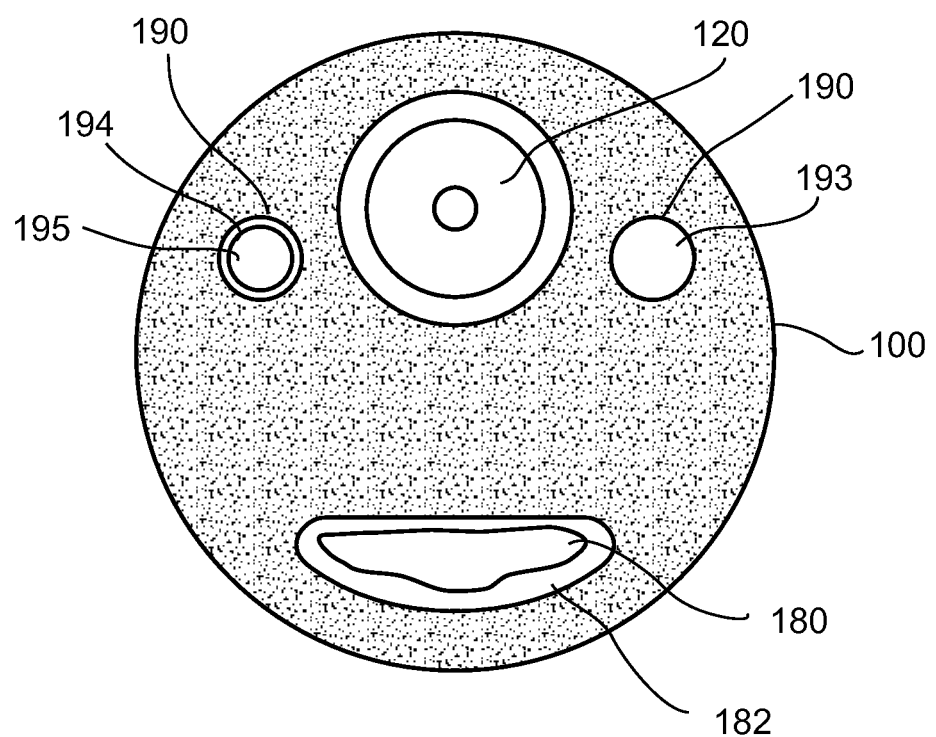
FIG. 3 is a simplified schematic of an end view of the endoscope tip of FIG. 1, according to an embodiment of the present invention.

Attention is now drawn to FIGS. 1, 2 and 3, which are simplified schematics of a cross-sectional side view, cross-sectional rear view and end view respectively of an endoscope tip, according to an embodiment of the present invention. These Figures illustrate an endoscope tip constructed of a unitary housing within which optical and electronic components are mounted directly, absent some intervening subassemblies usually used for holding, organizing or containing the components.

FIG. 1 shows an endoscope tip 100 which comprises an external housing 150 comprising at least a portion of outer wall 158 of tip 100. Housing 150 may be a unitary (undivided) component, or may have a split or divided design enabling to open housing 150 during construction of tip 100 to facilitate mounting of various components therein.

Housing 150 comprises a plurality of shaped lumens formed to accommodate various optical and electronic components mounted directly within the lumens. Housing 150 may be fabricated using standard electro-erosion (wire EDM and sinker EDM) and/or other standard manufacturing techniques suitable for metallic parts or other materials. High precision fabrication and tight tolerances are desirable for this component, but may be achieved by use of standard and well-known machining techniques or other methods known in the art. Casting and molding are other methods of fabrication suitable for producing endoscope tip 100, and metal, ceramics and plastics are among the materials appropriate for this purpose.

FIG. 1 shows an objective lens assembly 120 mounted directly within a lens mounting portion 130 of appropriate shape and size formed within housing 150. Objective lens assembly 120 comprises one or more lenses 122 and optional spacers 124. Prior art designs utilize space-taking sub-assembly elements serving only to contain and align sub-assemblies such as lens assembly 120. Accurate design and fabrication of lens mounting portion 130 within housing 150, and accurate design and fabrication of lens and spacer components of lens assembly 120, enables to eliminate these sub-assembly elements and to mount components of lens assembly 120 directly into mounting portion 130 (also called lumen 130) within housing 150. Direct mounting of elements of lens assembly 120 in lens mounting portion 130 of housing 150 enables to construct an optical system characterized by high performance, because space that would in prior art designs be taken up by sub-assembly container elements may, in endoscope 100, be devoted to large or complex lens designs, expanded sensor arrays, and other enhancements described hereinbelow, providing such advantages as higher resolution, wider angle of view, and/or larger aperture for light gathering, as compared to endoscopes of similar external size constructed according to prior art designs.

An exemplary configuration shown in FIG. 1 comprises 3 lenses labeled 122a, 122b, and 122c, and 3 spacers labeled 124a, 124b, and 124c. This configuration is exemplary only: other combinations of more or fewer components may be used.

Mounting of lenses and spacers directly into an outer housing 150 of endoscope tip 100, rather than into an intermediate lens tube or frame which must then be installed within outer housing 150, enables reduction of cross-sectional size of the endoscope tip in which camera and lenses are mounted.

In an exemplary embodiment of the invention, the diameter of endoscope tip 100 is between 0.7 mm and 7 mm, for example, between 2 and 4 mm, for example 3.3 mm. In an exemplary embodiment of the invention lens 122a has a diameter between 0.25 mm and 3 mm, for example between 0.75 mm and 1.5 mm, for example 1.2 mm. In an exemplary embodiment of the invention the smaller lenses of lens array 120 have a diameter between 0.15 mm and 2 mm, for example between 0.5 mm and 1 mm, for example 0.8 mm. In an exemplary embodiment of the invention sensor array 170 might be a square array between 0.5 mm square and 5 mm on a side, for example between 1.2 mm and 2.5 mm square, for example 2 mm on a side. If we consider as an example an exemplary embodiment containing a square sensor array 170 2 mm on a side, a lens array 120 with lenses between 1.2 mm and 0.8 mm, and an overall diameter of 3.3 mm, we may approximately estimate that the diameter of an endoscope tip containing these components in similar arrangement but constructed according to the methods of prior art would be larger by between 0.2-0.4 mm, because of the thickness of intermediate walls used in prior art designs for containing and organizing the internal components.

Alternatively, the space saved can be used to enhance endoscope performance. For example, the freed space can be used, for a given cross-section, to increase resolution of images which can be provided by a camera-based visualization mechanism by using a larger sensor array. Visualization performance can also be improved by utilizing larger or more complex optical elements (e.g. lenses) for a given cross-sectional tip size. Light output can be increased by utilizing larger bundles of optical fibers for illumination or by providing tip mounted LEDs for illumination. Fluid flow (for irrigation, suction, insufflation, lens-cleaning, etc.) can be increased by using larger diameter fluid lumens. Working channels of increased size enable to accommodate passage of larger size surgical and diagnostic instruments. These and other improvements are made possible by direct mounting of lens assembly 120 (and other components discussed hereinbelow) directly into lumens of housing 150.

In a method of construction according to an embodiment of the present invention, individual lens and spacer components are packed within lens mounting portion 130 by positioning and circumferentially gluing (or otherwise fixing in position) a first component (e.g. lens 122a), then positioning (without gluing) additional components (lenses and/or spacers) one after another, in order as required by a desired objective lens design, along lens mounting portion 130. The components are packed sufficiently tightly so that components are contiguous one to another. Then, the final component (e.g. 1 spacer 124c) is glued or otherwise fixed into position, thereby immobilizing all elements of lens assembly 120.

In a similar and alternative process, the lumen within which lens assembly 120 is to be assembled may be provided with a 'stop' feature 129 (e.g. a distal wall, a projection from a lateral wall, an inserted object) which limits advancement of another component (e.g. lens 122c) at a desired point within lumen 130. In this alternative method the another component is simply advanced along lumen 130 until the stop feature prevents further movement, additional components are introduced one after another along lens mounting portion 130 in order as required and packed contiguously, and then a final component (e.g. lens 122a) is glued or otherwise fixed into position, thereby immobilizing all elements of lens assembly 120.

These assembly processes are advantageous in that manufacturing according to these methods is faster and more convenient than gluing or otherwise attaching each element to the housing or to the adjoining elements. It is noted however that in some cases gluing or otherwise fixing elements to each other or to housing 150 may be considered appropriate, and is included within the scope of the invention.

Imaging sensor 170 may also be mounted directly in an interior lumen of housing 150 of endoscope tip 100.

Optionally, precision fabrication of internal lumen surfaces is used. In some embodiments precision fabrication of visualization system elements (e.g. lens assembly 120, imaging sensor 170) and also of the lumen surfaces which determine the installed position of the visualization system elements when those elements are mounted flush against those surfaces, enable production of a visualization system which requires little or no calibration. Precision matching of surfaces means that that imaging sensor 170, when mounted, will be in proper alignment with objective lens elements 120 as mounted. In some embodiments such assemblies require no calibration on some axes and little or no calibration on other axes. If, in the embodiment presented in FIGS. 1-3, the visualization system elements and the lumen surfaces against which they are mounted are fabricated with precision, the resultant visualization system will require calibration in at most only one dimension, and in some embodiments will require no calibration at all. For example, calibration or focusing of the embodiment presented in FIG. 1 may be accomplished by placing sensor 170 against upper shelf support 171 (or alternatively, against a wall of the housing) and then is moved forward or backward (left or right on FIG. 1 to accomplish focusing or calibration. No other adjustment or calibration is needed. Reduction of the need to calibrate the optical elements is an improvement over prior art manufacturing processes, saving time and enhancing reliability.

Additional visualization system elements may be similarly fabricated and installed. For example, FIG. 1 shows an optional lightpath-bending element 161 used to bend the light path to enable mounting sensor array 170 in a space-saving position. In this exemplary embodiment lightpath-bending element 161 is implemented as an optional prism 160. Prism 160 may similarly be fabricated to precision standards and mounted on a precision-fabricated lumen wall. Prism 160 may for example be glued onto a surface of imaging sensor 170 or glued into position within a somewhat enlarged cavity 131 which is an extension of the lumen formed by lens mounting portion 130, cavity 131 being in precise alignment with the central optical axis formed by lens mounting portion 130. Electronic light-sensor array 170 may similarly be glued within an additional cavity 132 similarly provided within housing 150, as shown in FIG. 1. Alternatively, light-sensor array 170 may be mounted perpendicular to the central axis of lens mounting portion 130, eliminating the need for prism 160.

Endoscopes often comprise light guide fiberoptic bundles used for illuminating the visual field of the endoscope. According to embodiments of the present invention, these light guide fiberoptic bundles are also directly mounted within and directly attached to housing 150, without outer tubes or other constraining structures containing the bundles or forming the bundles' distal ends. This construction strategy also enables further reduction of the cross-sectional area of the endoscope tip, or alternatively, for a given cross-sectional size, allows for addition of more fibers in the illuminating bundle thereby enhancing visualization performance provided by the endoscope.

In an embodiment shown in FIGS. 1 and 2, light-guiding optical fiber bundles 180 are provided and enable one to illuminate tissues and other objects within the field of view of lens assembly 120. Optical fiber bundles 180 are inserted directly into lumens 182 provided within housing 150, and may be fixed directly therein by gluing or other means. As discussed hereinabove with respect to lens mounting portion 130, lumens 182 may be produced by machining processes applied to housing 150, or by various other means. Light-guide fiber bundles 180 and lumens 182 are more clearly seen in FIG. 2. For clarity of the Figures, a spatial separation has been shown between bundles 180 and lumens 182, yet in practice bundles 180 may completely fill lumens 182. Additionally, lumens 190 shown in FIGS. 2 and 3 may be used to hold additional light-guide fiber bundles providing multi-source illumination.

Gluing is a convenient means for fixing individual components within housing 150, yet other means may be used. For example, elements such as the lenses or prisms could be press-fit into place, or optical elements having a metallic coating could be brazed into place. Alternatively, elements may be held in place mechanically with a capturing element.

In an optional alternate construction, one or more lumens, examples of which are labeled 190 in FIGS. 2-3, may be configured as working channels 194 through which surgical or diagnostic tools (e.g. tool 195) may be advanced through endoscope tip 100 and into body tissues. Thus, endoscope tip 100 may comprise one or more lumens 182 comprising light-guiding fiberoptic bundles 180, one or more lumens 190 serving as working channels for introduction of surgical instruments into body tissues, both, or neither. Lumens 190 may also be configured as fluid channels 193, enabling passage of fluids into or out of the body through endoscope tip 100. For example, a fluid channel 193 may be used to irrigate a treatment area, thereby facilitating viewing of that area.

Attention is now drawn to FIG. 3, which is a simplified schematic providing an end-on view of endoscope tip 100, according to an embodiment of the present invention. FIG. 3 shows a distal end of objective lens 120, a light-guide lumen 182 and light-guide fiber bundle 180, a working channel 194, and a fluid lumen 193.

In an exemplary method of assembly, lens mounting portion 130, cavity 131, upper shelf support 171 or lower shelf support 172 for sensor array 170, and other internal features are first fabricated in housing 150. Lenses and intervening spacers of assembly 120 are then inserted in proper sequence into lens mounting portion 130, as described above. Once these optical components are properly inserted and positioned, optical adhesive or other suitable adhesive, for example a glue which sets with exposure to ultraviolet light, or any other suitable means, can be used to secure objective lens assembly components 120. Since gluing is around the periphery of the optical elements, where light rays do not pass, standard techniques for assembly and gluing can be used. Next, an imaging sensor assembly 170 is inserted into housing 150, and accurately positioned onto interior surface shelf 171 to achieve proper focus, as described above. Imaging sensor assembly 170 may comprise any electronic imaging sensor array, and may for example be a CCD sensor array, a CMOS sensor array, or a sensor array using other electro-optical imaging technology.

Adhesive may be used to secure sensor assembly 170 directly to interior surface shelf 171. Alternatively, imaging sensor assembly 170 may be positioned and fixed onto interior surface shelf 172. Whichever interior surface (e.g. shelf 171 or shelf 172) is used to mount imaging sensor array 170, that surface should be precisely aligned with lens mounting portion 130, thereby ensuring correct positioning of all parts of the visualization system's optical and imaging components. Light guide bundles 180 can be installed either before or after installation of lens components 120 and sensor array 170, as determined by convenience within the assembly process.

Figure 4:
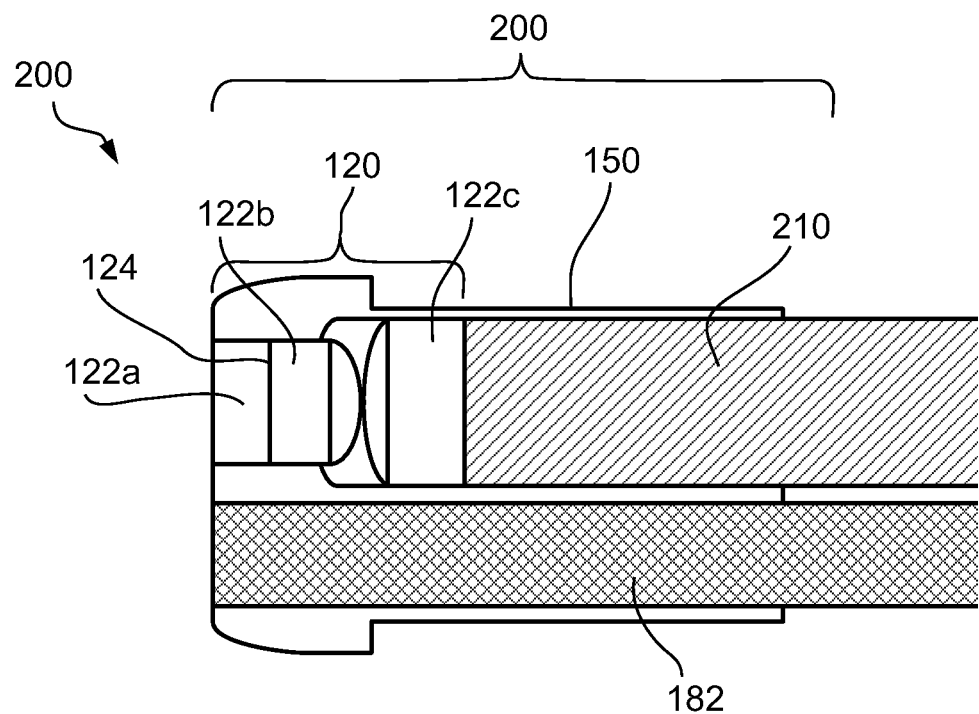
FIG. 4 is a simplified schematic of a cross-sectional side view of a fiberoptic endoscope, according to an embodiment of the present invention.
Figure 5:
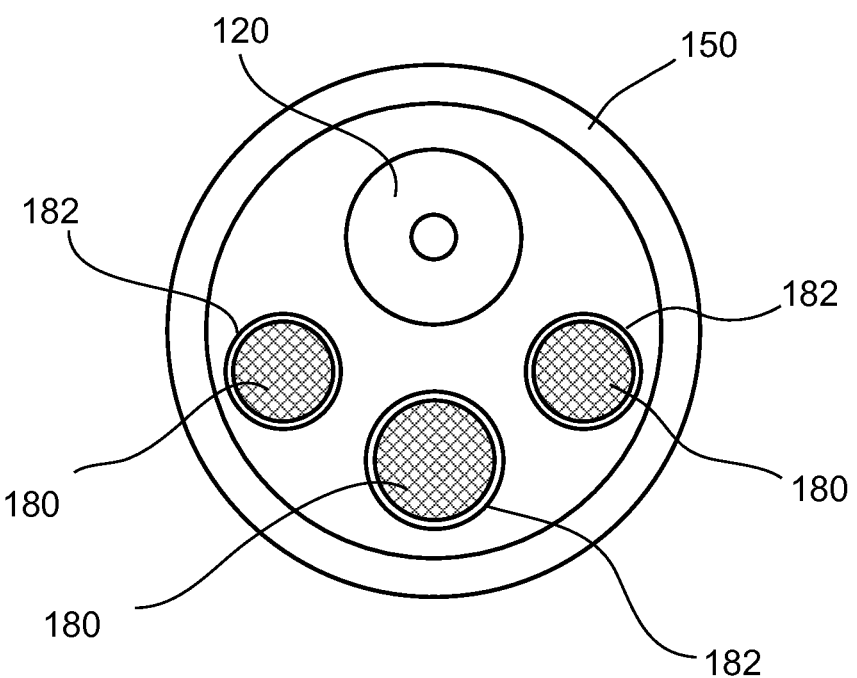
FIG. 5 is a simplified schematic of an end view of the fiberoptic endoscope of FIG. 4, according to an embodiment of the present invention.

As used herein, the term "fiberoptic endoscope" is used to refer to endoscopes wherein a coherent fiberoptic bundle is used for transmission of an image to an optical eyepiece, as an alternative to use of an electronic image sensor 170 to detect and electronically transmit the image. Attention is now drawn to FIGS. 4 and 5, which are simplified schematics showing side cross-sectional and end views respectively of a fiberoptic endoscope 200, according to an embodiment of the present invention.

In fiberoptic endoscope tip 200, a coherent image-guide fiberoptic bundle 210 is mounted directly within housing 150, without intervening tube or container, according to an embodiment of the present invention.

As discussed above with respect to endoscope 100, direct mounting of objective lens components 120 and fiberoptic bundle 210 into housing 150 can reduce construction complexity as compared to prior art construction techniques, and can save space. This saving of space can be applied to reducing cross-sectional area of the endoscope tip, or can be used to enhance performance by providing larger or more complex optical elements. For example, space saved by direct mounting of bundle 210 into housing 150 can be used to increase optical performance by increasing size and/or complexity of the objective lens elements, or can be used to increase the number of fibers in the coherent fiberoptic image bundle, thereby enhancing resolution of images.

In an exemplary embodiment of the invention, a coherent fiberoptic image bundle such as bundle 210 is first formed in a separate manufacturing process external to endoscope tip 200. As is customary in fabrication of such bundles, the individual fibers in the bundle are optionally fused together during the fiber drawing process. In endoscope fabrication processes typical in prior art, the coherent fiberoptic bundle is installed in the endoscope with the internal fusing structure and/or an encapsulating material intact. However, according to some embodiments of the present invention, during the process of installing the bundle in the endoscope the internal fusing structure which holds the individual fibers together is removed by dissolving away the fusing material except for the fusing material at the ends of the bundles. During this process, to preserve coherence of the bundle, encapsulating tubes are typically placed over the ends of the coherent bundle before the fusing structure is removed. In some embodiments of the present invention, the encapsulating tube over at least one end of the bundle is removed (dissolved by acid or other chemical, for example), yet leaving the internal fusing structure of the end of the bundle intact, before coherent image bundle 210 is inserted into housing 150. In this manner, coherence is preserved, yet space is saved because the Encapsulating tube positioned over the end of the bundle during bundle preparation is not installed in the endoscope tip.

Table 1 (below) is provided to demonstrate some advantages of methods of endoscope assembly according to embodiments of the present invention. It is noted that Table 1 is provided for exemplary purposes only, and is not intended to be limiting nor should Table 1 be understood as describing all prior art assembly process, nor all assembly process which are according to embodiments of the present invention. However, it may be seen from Table 1 that construction of endoscope 100 according to embodiments presented herein generally requires fewer parts and fewer manufacturing actions than are required by endoscope tip construction according to methods of prior art.

As explained in detail hereinabove, in Procedure 1 in some embodiments of the present invention lenses and spacers comprising an objective lens array may be mounted directly into housing 150, rather than being mounted into a lens tube or other container.

According to processes described above, gluing of objective lens array elements may also be simplified as shown in Table 1 with respect to Procedure 2. Prior art procedures 5, 6, and 7 of Table 1 are made unnecessary in some embodiments of the present invention, since in some embodiments of the present invention there is no lens tube and no imaging sensor frame, lens and sensor elements being mounted directly in housing 150. Calibration of the assembled product also tends to be simpler in embodiments of the present invention, in that according to methods of prior art, alignment and focus of a sensor assembly fulfilling the role of sensor assembly 170 must take into account three axes of focus and alignment. In contrast, in some embodiments of the present invention positions and orientations relevant to the alignment and focus of optical components with respect to sensor elements are substantially determined by the positioning and orientation of the internal lumen surfaces of external housing 150, together with accurate production of external surfaces of elements to be installed in housing 150. In consequence, in some embodiments of the present invention only one axis of focus is involved in methods of construction of endoscope 100 according to embodiments of the present invention.

TABLE 1

Comparison of Assembly Steps for Prior Art Endoscope Tips and for endoscope tips according to some embodiments of the present invention

| Procedure | Assembly process according to prior art | Assembly process according to an embodiment of the present invention |
|---|---|---|
| 1 | Insert lenses & spacers into Lens Tube | Insert lenses & spacers into lens mounting portion of Endoscope Tip |
| 2 | Glue lenses & spacers in place in Lens Tube | Glue lenses & spacers in place. In some Tube embodiments some of these elements need not be individually glued. |
| 3 | Assemble imaging sensor and electronics onto PCB | Assemble imaging sensor and electronics onto PCB |
| 4 | Mount prism onto imaging sensor | Mount prism onto imaging sensor |
| 5 | Attach electronics PCB assembly onto imaging sensor frame | |
| 6 | Insert Lens Tube into Distal Tip and align and/or focus as required | |
| 7 | Glue Lens Tube into place | |
| 8 | Insert imaging sensor frame into Distal Tip | Insert Sensor Assembly into Endoscope Tip |
| 9 | Align & focus Sensor Assembly (3 axis alignment/focus) | Focus Sensor Assembly (only 1 axis focus required, no alignment problem) |
| 10 | _Secure Sensor Assembly in place | Secure Sensor Assembly in place |

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An endoscope tip comprising:
a housing of unitary construction and defining an external surface of the endoscope tip,
wherein the housing defines a lumen at a first internal surface of the housing, the lumen configured to mount an optical element assembly by direct mounting of a first component of the optical element assembly with the first internal surface and a final component of the optical element assembly with the first internal surface such that the first component and the final component prevent movement of one or more intermediate components of the optical element assembly, the optical element assembly including the first component and the final component on opposite sides of the one or more intermediate components along an optical axis, and
wherein the housing comprises a lower shelf support at a second internal surface of the housing and continuous from a material that defines the lumen, the lower shelf support being configured for direct mounting of an optical sensor array to the second internal surface for optical association with the optical element assembly received by the lumen.

2. The endoscopic tip of claim 1, wherein the lower shelf support defines a mounting surface for the direct mounting of the optical sensor array, the mounting surface having a normal direction that is perpendicular to the optical axis.

3. The endoscopic tip of claim 1, wherein the housing further defines an enlarged cavity at a third internal surface of the housing, the enlarged cavity adjacent the lumen and configured to receive a prism.

4. The endoscopic tip of claim 3, wherein:
the enlarged cavity is substantially continuous with the lumen, and
the lower shelf support extends substantially parallel to and offset from the lumen within the housing.

5. The endoscopic tip of claim 1, wherein the housing further comprises a plurality of other lumens with a first of the plurality of other lumens being configured for direct mounting of a fiberoptic bundle.

6. The endoscopic tip of claim 5, wherein a second of the plurality of other lumens is configured for one or both of:
directing a surgical or diagnostic tool toward a distal end of the endoscopic tip; or
directing fluid flow toward the distal end.

7. The endoscopic tip of claim 1, wherein:
the endoscopic tip further comprises
the optical element assembly, and
one or both of the first component or the final component of the optical element assembly is glued to the first internal surface.

8. The endoscopic tip of claim 7, wherein the one or more intermediate components is immobilized by the direct mounting of the first component and the final component with the first internal surface, and wherein the one or more intermediate components are free of glues or lens tubes.

9. An endoscope tip comprising:
a housing of unitary construction and defining an external surface of the endoscope tip,
wherein the housing defines a first lumen at a first internal surface of the housing, the first lumen configured to mount an optical element assembly by direct mounting of a first component of the optical element assembly with the first internal surface and a final component of the optical element assembly with the first internal surface such that the first component and the final component prevent movement of one or more intermediate components of the optical element assembly, the optical element assembly including the first component and the final component on opposite sides of the one or more intermediate components along an optical axis,
wherein the housing further defines a second lumen at a second internal surface of the housing, the second lumen configured to receive a fiberoptic bundle for direct mounting of the fiberoptic bundle to the second internal surface.

10. The endoscopic tip of claim 9, wherein the housing comprises a lower shelf support continuous from a material that defines the first and second internal surfaces, the lower shelf being arranged substantially between the first and second lumens.

11. The endoscopic tip of claim 10, wherein the lower shelf support is configured for direct mounting of an optical sensor array thereon.

12. The endoscopic tip of claim 11, wherein the optical element assembly and the optical sensor array are directly mounted to the housing such that the optical axis of the optical element assembly and an optical axis of the optical sensor array are perpendicular to one another.

13. The endoscopic tip of claim 9, wherein the first internal surface forms an obstructive feature in the first lumen, the obstructive feature formed form a material that defines both the external surface and the first internal surface, the obstructive feature defining a narrowest diameter of the first lumen and establishing a stop feature that limits advancement of the optical element assembly therethrough.

14. The endoscopic tip of claim 9, further comprising the fiberoptic bundle glued to the second internal surface.

15. The endoscopic tip of claim 14, wherein the endoscopic tip is free of any outer tubes or constraining structures between the fiberoptic bundle and the external surface, thereby maximizing fiberoptic bundle density within the endoscopic tip.

16. An endoscope tip comprising:
a housing of unitary construction and defining an external surface of the endoscope tip,
wherein the housing comprises:
an upper shelf support at a lens mounting portion of the housing, wherein the lens mounting portion is configured to mount an optical element assembly by direct mounting of a first component of the optical element assembly with the upper shelf support and a final component of the optical element assembly with the upper shelf support such that the first component and the final component prevent movement of one or more intermediate components of the optical element assembly, the optical element assembly including the first component and the final component on opposite sides of the one or more intermediate components along an optical axis, wherein one or more of the intermediate components or the final component being free from glues or lens tubes, and
a lower shelf support below the lens mounting portion and adjacent an additional cavity of the housing, the lower shelf support continuous from a material forming the upper shelf support and the external surface of the housing, wherein the additional cavity is configured to receive an optical sensor array for direct mounting of the optical sensor array to the lower shelf support.

17. The endoscopic tip of claim 16, wherein the housing defines:
a first lumen forming the lens mounting portion, and
a second lumen configured to receive a fiberoptic bundle for direct mounting of the fiberoptic bundle thereon.

18. The endoscopic tip of claim 17, wherein:
the endoscopic tip further comprises:
the optical element assembly,
the optical sensor array, and
the fiberoptic bundle; and
each of the optical element assembly, the optical sensor array, and the fiberoptic bundle are glued directly to the housing.

19. The endoscopic tip of claim 16, wherein the housing further defines an enlarged cavity configured to receive a prism for direct mounting of the prism to an image sensor within the housing.

20. The endoscopic tip of claim 19, wherein the prism establishes optical association of the optical element assembly and the optical sensor array.

* * * * *